US00PP22649P3

(12) United States Plant Patent
Roose et al.

(10) Patent No.: US PP22,649 P3
(45) Date of Patent: Apr. 17, 2012

(54) MANDARIN TREE NAMED 'FAIRCHILDLS'

(50) Latin Name: *Citrus reticulata*
Varietal Denomination: FairchildLS

(75) Inventors: Mikeal L. Roose, Riverside, CA (US); Timothy E. Williams, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 88 days.

(21) Appl. No.: 12/590,763

(22) Filed: Nov. 12, 2009

(65) Prior Publication Data

US 2011/0113518 P1 May 12, 2011

(51) Int. Cl.
*A01H 5/00* (2006.01)

(52) U.S. Cl. ..... Plt./201; Plt./202

(58) Field of Classification Search ..... Plt./202, Plt./201
See application file for complete search history.

*Primary Examiner* — Kent L Bell
(74) *Attorney, Agent, or Firm* — Kilpatrick Townsend & Stockton LLP

(57) ABSTRACT

'FairchildLS' is a mid-season maturing diploid mandarin that combines medium-large sized fruit of excellent quality and production, with low seed content even in mixed plantings. It would likely be successful in the mid to late-season marketing window that currently has very few low seeded cultivars.

6 Drawing Sheets

Latin name of the genus and species: The mandarin cultivar of this invention is botanically identified as *Citrus reticulata.*

Variety denomination: The variety denomination is 'FairchildLS'.

BACKGROUND OF THE INVENTION

This invention relates to a new and distinctive mandarin cultivar designated 'FairchildLS', which was developed at Riverside, Calif. and derived from an irradiated bud of 'Fairchild' mandarin. 'Fairchild' mandarin was produced by J. R. Furr in Indio, Calif. from a conventional hybridization of 2n Clementine 'Algerian' mandarin×2n 'Orlando' tangelo (itself a hybrid of 'Duncan' grapefruit×'Dancy' mandarin produced in Florida). 'Fairchild' was released in 1964.

Irradiation of budwood of 'Fairchild' mandarin, taken from registered trees in Lindcove, Calif., was accomplished in June, 1997 at Riverside using 50 Gray units of gamma irradiation from a Cobalt-60 irradiation source. Buds from this irradiation were propagated onto various rootstocks in the greenhouse at Riverside where they were grown to field-plantable-sized trees. These trees were planted in June 1998 at Riverside. Fruit production and evaluation on these trees began in 2001. One selection from this irradiated population (propagated on Carrizo citrange rootstock) distinguished itself from the others in having very low seed counts in comparison to the original 'Fairchild' cultivar, as well as having the excellent fruit quality and normal fruit production characteristics of the 'Fairchild' parent (see, FIGS. 1 and 2). This selection, later designated 'FairchildLS', was known throughout experimental evaluation as 'Fairchild' IR2 (for 'Fairchild' IRradiated selection #2). After two seasons of fruiting this selection, 'Fairchild IR2', was selected for further trials and in June 2002, buds were taken from this selection and propagated onto Carrizo and C35 citrange rootstocks at Riverside. In April 2003 budwood from this selection was sent to Riverside, Calif. for evaluation of disease status and elimination of viruses and other pathogens, as needed.

Twenty trees, propagated from budwood taken from the "mother" tree selection were planted at Riverside in June 2003. Fruit production on these twenty trees commenced in 2006. In June 2005 two trees of 'FairchildLS', which had been produced from budwood tested and certified as tristeza-free, were sent to Lindcove, Calif. where they were planted in the *citrus* breeding block. Further propagations from the Riverside budwood source were made at Lindcove in the summer of 2003. In June 2004, twelve trees from this propagation were planted in Irvine, Calif. and two trees in Santa Paula, Calif. An additional forty-eight trees from this same 2003 propagation were planted in 2005 at four trial sites: Lindcove, Arvin, Oasis and Woodlake. All trials were propagated equally on Carrizo and C35 citrange rootstocks. Fruit production of these propagated trees commenced in 2006 (a few trees at two sites) and 2007 (most trees at most sites). The properties of 'FairchildLS' were found to be true to type and transmissible by asexual reproduction in comparing these plantings with the original 'FairchildLS' selection.

BRIEF SUMMARY OF THE INVENTION

'FairchildLS' is a mid-season maturing diploid mandarin that combines medium-large sized fruit of excellent quality and production, with low seed content even in mixed plantings. It would likely be successful in the mid to late-season marketing window that currently has very few low seeded cultivars.

BRIEF DESCRIPTION OF THE DRAWINGS

The Figures depict various characteristics of 'FairchildLS'.

DETAILED DESCRIPTION OF THE INVENTION

Figure 1:
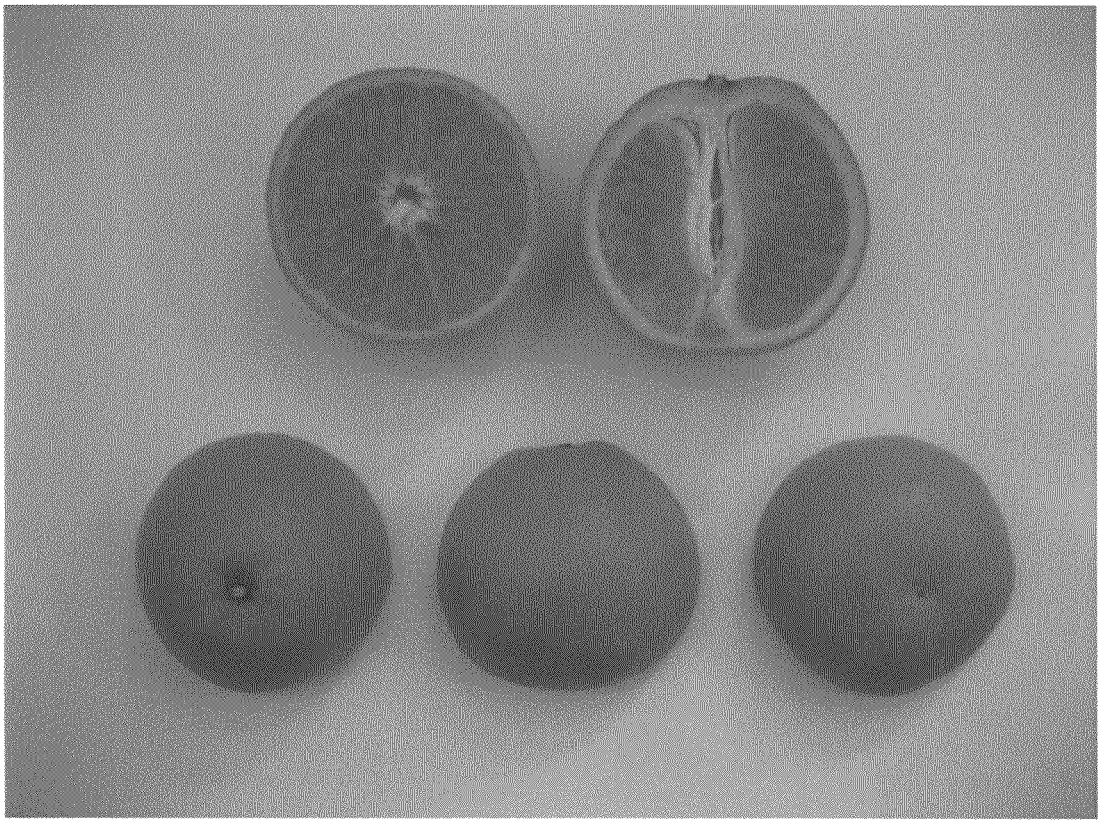
FIG. 1 shows fruit of 'FairchildLS' taken at Riverside in February 2009.
Figure 2:
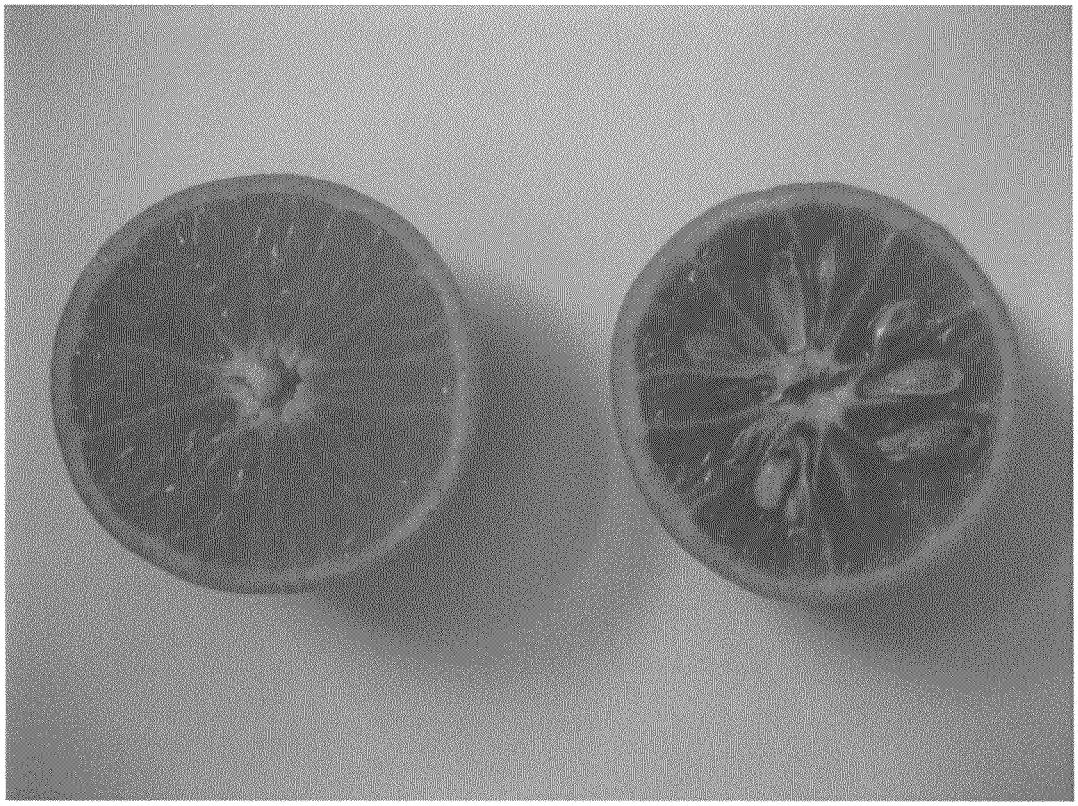
FIG. 2 shows a comparison of seed content of 'FairchildLS' (left) and standard 'Fairchild' (right) mandarins under cross-pollinated conditions.

'FairchildLS' is a mandarin selection developed at Riverside, Calif. from an irradiated bud of the diploid mandarin cultivar 'Fairchild', which is a mid-season maturing variety. Evaluation of 'FairchildLS' began on the original tree at Riverside in 2001 and has continued annually until the present. Tree size, growth, as well as fruit production and fruit quality characteristics, have been compared in these evaluations to 'Fairchild' mandarin from the same field block. Three, four and five-year-old 'FairchildLS' trees in trials at Riverside, Irvine, Arvin, Lindcove, Oasis and Woodlake have also been evaluated from two to four years of fruiting (see Tables 1 and 2).

'FairchildLS' distinguishes itself by being low seeded (2.4 seeds/fruit) in all situations of cross-pollination, differing from 'Fairchild', which will have up to 15-25 seeds/fruit in cross-pollinated situations. In Riverside, Calif. 'FairchildLS' matures in winter, typically early January, and holds its fruit quality characteristics through late March. Fruit size is moderately large (64 mm in diameter) averaging 110 grams per fruit. Fruit are deeply oblate in shape with a deep orange rind color and a moderately smooth rind texture. Flesh color is deep orange and finely textured, and the fruit are moderately easy to peel. Fruit are juicy, with a rich, sweet flavor when mature. Tree growth habit is rounded, producing a dense, compact tree crown with excellent production commencing in the third year after planting. 'FairchildLS', like its parent 'Fairchild', may need a pollinizer for best production. 'FairchildLS' is well adapted to growing in all California climate zones normally associated with *citrus*, including hot desert areas (where maturity and marketing occur in November-December), which is a rare and distinct advantage for a mandarin. Alternate bearing does exist, but can be controlled with appropriate cultural practices.

'FairchildLS' mandarin can be grown according to accepted cultural practices for most mandarin varieties, including planting densities of 180-300 trees per acre, normal fertilization and pest control practices, and the use of standard rootstocks for mandarins. Pruning is not normally necessary since the normal growth habit of the tree results in a dense, compact crown. However, selective interior pruning may enhance production and health of the tree if applied after the second year of full fruit production and regularly thereafter. Other rootstocks adapted to more marginal growing conditions of salinity, high pH or very heavy soils, including the lemon types *C. macrophylla,* Volkameriana, and rough lemon, may be useful in those conditions but overall fruit quality would likely be affected negatively. Sour orange or mandarin type rootstocks such as Cleopatra might be more suitable in these marginal conditions since fruit quality would not be affected to the extent the lemon-type rootstocks impart.

Comparison with Existing Mandarins

Mid to late season maturing mandarin cultivars in production include 'Fairchild' mandarin (the original cultivar from which 'FairchildLS' was derived), 'Murcott' tangor, 'Fortune' mandarin, 'Ortanique' tangor, 'Page' mandarin 'Temple' tangor, as well as late-maturing Clementina selections including 'Hernandina' and 'Nour', 'Dancy' mandarin and 'Minneola' tangelo. All of these cultivars will be seedy if grown in the presence of a pollenizer. Some, including the Clementina selections, 'Fortune', 'Ortanique' and 'Page' mandarins will have few seeds if no pollinizer is present. Recently released mid and mid-late season cultivars that are very low-seeded include 'Tango' mandarin, 'Gold Nugget', 'TDE2' mandarin hybrid (Shasta Gold®) 'TDE3' mandarin hybrid (Tahoe Gold®), and 'TDE4' mandarin hybrid (Yosemite Gold®) and 'DaisySL' mandarin. 'FairchildLS' differs from these cultivars in being slightly earlier maturing and better adapted to hot desert climates than all but 'DaisySL'. Trees of 'FairchildLS' tend to be smaller than all the other varieties except 'DaisySL'. Additional differences (summarized in Table 6) distinguish it from each of these cultivars.

'FairchildLS' mandarin exhibits low seed numbers (2.4 seeds per fruit) in all fruit under all conditions of cross-pollination. Additionally, preliminary evaluations indicate that pollen from 'FairchildLS' has reduced germination rates in culture (~25%) and is therefore likely to reduce the tendency to cause seeds in other mandarins, causing few seeds in selected Clementine mandarin and 'W. Murcott' mandarin cultivars when hand pollinated onto those selections. A comparison of 'FairchildLS' with other low-seeded late-season mandarins is provided in Table 6 below. 'FairchildLS' is distinctive and superior in having a very wide climatic growing area, somewhat less alternate bearing, and fruit appearance that may be preferred in some markets.

The Royal Horticultural Society (R.H.S.) color numbering system is used herein for the color description of the rind, seed, bark, leaf, flower, flesh color and other interest of the 'FairchildLS' mandarin cultivar.

Trees, Foliage, and Flowers

Figure 3:
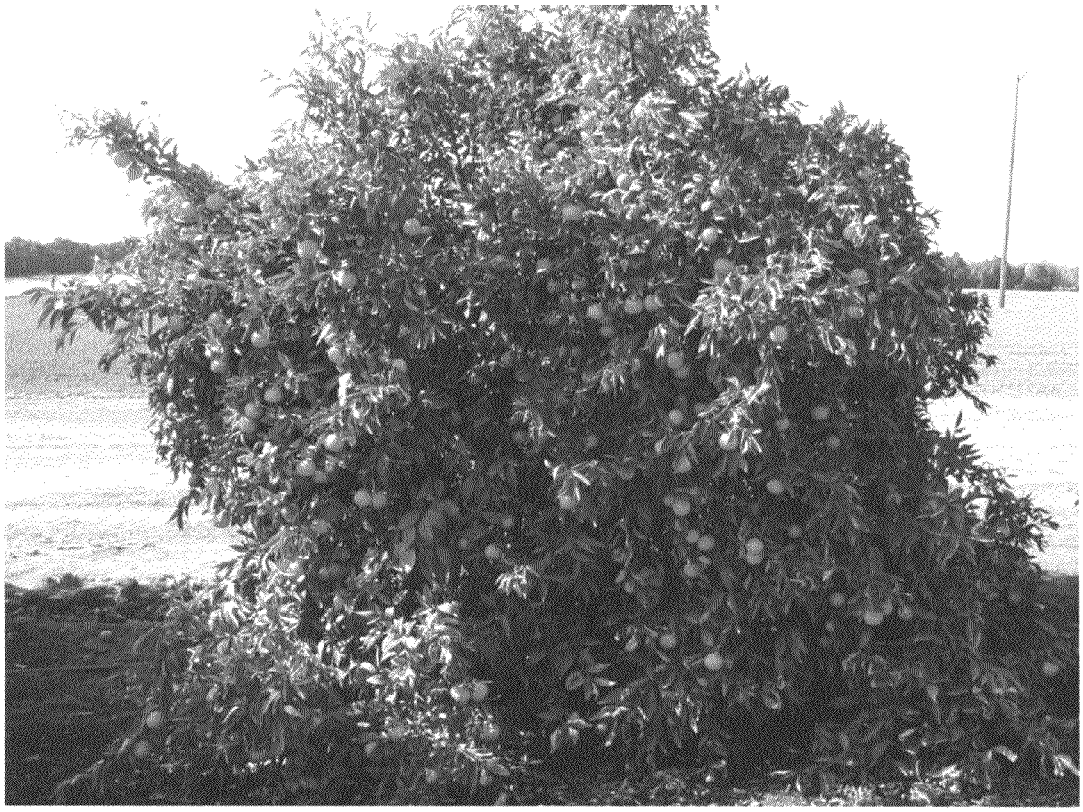
FIG. 3 shows an eleven-year-old "mother" tree of 'FairchildLS' on Carrizo citrange rootstock.
Figure 4:
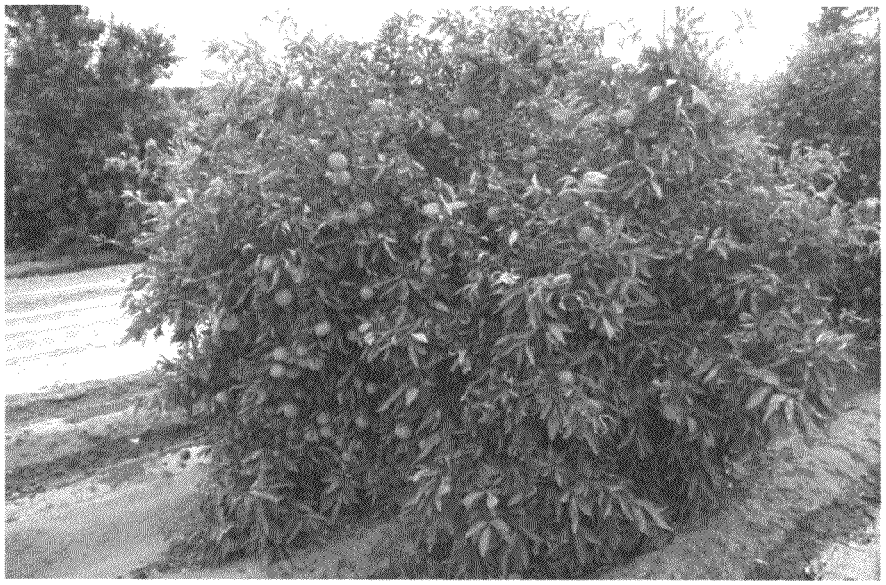
FIG. 4 shows a five-year-old 'FairchildLS' tree on Carrizo citrange rootstock at Riverside, Calif.
Figure 5:
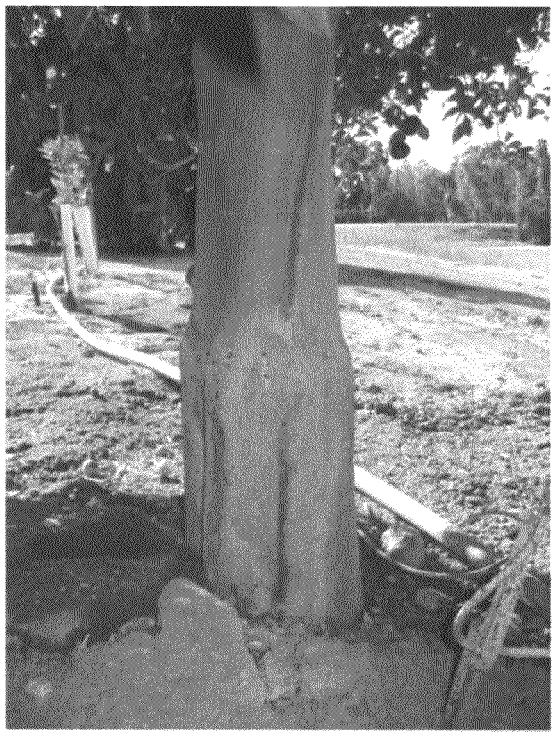
FIG. 5 shows the bud-union of an eleven-year-old 'FairchildLS' on Carrizo citrange rootstock.

Tree size and growth characteristics of 'FairchildLS' have been consistent with 'Fairchild' throughout the evaluations. Growth of both the 'Fairchild' and the 'FairchildLS' selection has been generally rounded and somewhat spreading in the first four years, followed by a tendency to grow into a more compact, dense rounded crown in ensuing years. The eleven-year-old 'FairchildLS' "mother" tree at Riverside on Carrizo citrange rootstock is 2.7 m high and 3.0 m wide with a rounded, compact growth habit yielding a canopy volume of 12.72 $m^3$ (FIG. 3) with a scion circumference of 37.9 cm and a rootstock circumference of 52.4 cm (FIG. 5). In comparison, eleven-year-old 'Fairchild' control trees on 'Carrizo' (from the same block as the 'FairchildLS' "mother" tree) have averaged 2.8 m tall and 2.9 m wide yielding a canopy volume of 12.33 $m^3$ on Carrizo citrange rootstock with a scion circumference of 36.9 cm and a rootstock circumference of 49.9 cm. In the younger multi-location trials, five-year-old 'FairchildLS' trees on Carrizo rootstock have averaged 2.5 m in height and 2.4 m in diameter with canopy volumes of 7.54 $m^3$ (FIG. 4). Trees on C35 rootstock averaged 2.4 m in height and 2.4 m in diameter with canopy volumes of 7.24 $m^3$. Diameter of the four scaffold branches at a point 15 cm from the trunk was measured and averaged 6.3 cm (values 5.1, 5.5, 7.0 and 7.5 cm).

Figure 7:
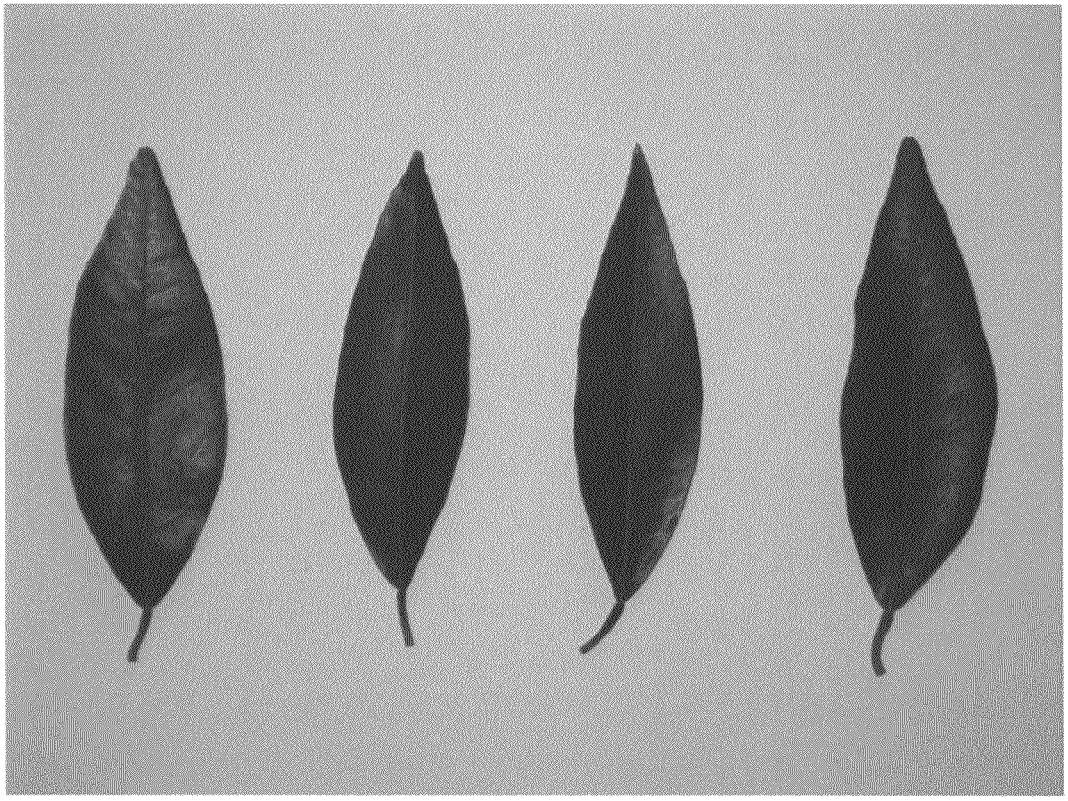
FIG. 7 shows leaves of 'FairchildLS'.

Leaves of 'FairchildLS' are lanceolate in shape and concave in cross section. They have an acute apex with weak emargination and an acute base, and are dark-green in color (FIG. 7). Petioles are short and normal, lacking wings. The selection further lacks thorns.

Figure 8:
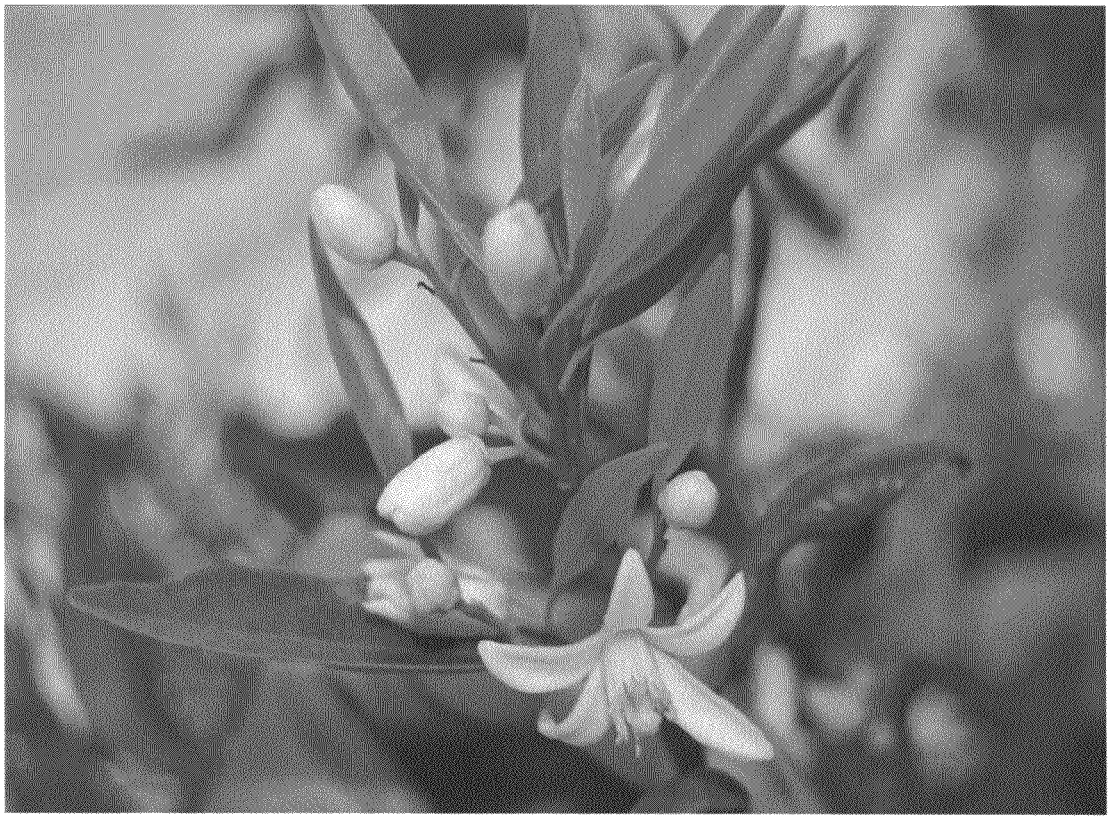
FIG. 8 shows open and closed flowers of the 'FairchildLS' mandarin cultivar.

Flowers of 'FairchildLS' are hermaphroditic with whitish petals (RHS Greenish White 157D) on both upper and lower surfaces, and yellowish (RHS Yellow 13C) anthers and are borne in clusters (FIG. 8). Pollen viability for 'FairchildLS' is low (25-35% germination) in comparison to 'Fairchild' (84% pollen germination) and pollen production is significantly reduced (about 20% of the quantity of pollen grains produced by 'Fairchild').

TABLE 1

Tree, leaf, flower and seed characteristics of 'FairchildLS' mandarin (for nine- to eleven-year-old tree or five-year-old tree)

| | |
|---|---|
| 1. Tree height (on Carrizo rootstock) | 2.7 m |
| 2. Crown diameter | 3.0 m |
| 3. Crown shape | Round, compact |
| 4. Scion circumference/rootstock circumference Ion Carrizo rootstock measurement taken at 15 cm above soil surface) | 38.5 cm/55.0 cm |
| 5. Scion circumference/rootstock circumference (on C35 rootstock) | 37.0 cm/53.0 cm |
| 6. Bud-union characteristics (citranges) | Slightly benched* |
| 7. Rootstock-scion compatibility | Excellent (with citranges) |
| 8. Tree vigor | Moderately vigorous |
| 9. Bark color | RHS Grey-Brown 199A |
| 10. Leaf shape | Lanceolate |
| 11. Leaf cross-section | Concave |
| 12. Leaf blade length | 80.8 mm |
| 13. Leaf blade width | 25.5 mm |
| 14. Leaf apex | Acute with weak emargination |
| 15. Leaf base | Acute |
| 16. Leaf margins | Very slightly crenate |
| 17. Leaf abaxial color | RHS Green 137A |
| 18. Leaf adaxial color | RHS Green 143A |
| 19. Petiole length | 10.6 mm ± 0.9 |
| 20. Petiole width | 1.6 mm |
| 21. Petiole wings | Absent |
| 22. Petiole color | RHS Green 137A |
| 23. Thorniness | Not present |
| 24. Inflorescence type | Clustered |
| 25. Flowering habit | Flowers once per year |
| 26. Flower size | 13.0 mm (medium) |
| 27. Flower structure | Complete |
| 28. Petal color | RHS Greenish white 157D |
| 29. Anther color | RHS Yellow 13C |
| 30. Pollen viability (germination in culture) | Low (25-35%) |
| 31. Pollen color | RHS Yellow 13C |
| 32. Scion diameter/rootstock diameter (on Carrizo rootstock measurement taken at 15 cm above soil surface) | 12 cm/18 cm |

*The term "benched" means that the scion diameter is considerably less than the rootstock diameter and that the angle of the tissue across the bud union is greater than 45°.

TABLE 1.1

Flower characteristics of 'FairchildLS' mandarin (for nine- to eleven-year-old tree or five-year-old tree)

| Characteristics | Mean | SD |
|---|---|---|
| petal number | 5 | 0 |
| petal length | 13.7 mm | 0.55 mm |
| petal width | 5.5 mm | 0.049 mm |
| petal shape | elliptic | |
| petal apex shape | obtuse | |

TABLE 1.1-continued

Flower characteristics of 'FairchildLS' mandarin (for nine- to eleven-year-old tree or five-year-old tree)

| Characteristics | Mean | SD |
|---|---|---|
| petal base shape | truncate | |
| petal margin | entire | |
| bud length | 12.2 mm | 0.24 mm |
| bud diameter | 5.7 mm | 0.043 mm |
| bud shape | linear | |
| bud color | 155D | |
| sepal number | 5 | 0 |
| sepal length - free | 1.66 mm | 0.11 mm |
| sepal width | 2.13 mm | 0.22 mm |
| Sepal shape (nonfused portion) | Deltoid | |
| Sepal apex | acute | |
| Sepal margin | entire | |
| Sepal color - abaxial | 1D | |
| Sepal color - adaxial | 1D | |

Fruiting, Fruit and Production Characteristics

Fruit of 'FairchildLS' are deeply oblate in shape with no neck. The fruit has a slightly concave basal end (moderately depressed) with a truncate (slightly depressed) distal end and a non-persistent style. The fruit is medium sized for a mandarin (classified as Large by State of California standards), averaging 64 mm in diameter and 56 mm in height. The fruit further has a smooth, deep orange rind color (RHS Orange N25B) and relatively inconspicuous, slightly depressed oil glands. The rind is of medium adherence at maturity and relatively thin, averaging 3.5 mm in thickness, which makes the fruit only moderately easy to peel. The fruit interior has a moderately fine flesh texture with 11-12 segments and a semi-hollow axis of medium size at maturity. The fruit are juicy, averaging 47% juice and average 110 g in weight. Fruit from trees on Carrizo citrange rootstocks averaged 12.1-13.0% soluble solids and 0.85-1.17% acid in January at four trial locations in California with soluble solids increasing to 13.2-14.5%, and acid decreasing to 0.76-0.93% by mid-March (Table 5). Fruit from trees on C35 citrange rootstocks averaged 11.2-12.8% soluble solids and 0.94-1.23% acid in January at four trial locations in California with soluble solids increasing to 13.1-14.0% and acid decreasing to 0.78-1.01% by mid-March. Fruit average 2.4±0.6 seeds per fruit in the presence of substantial cross-pollination pressure at all trial locations (summarized from Table 4). Seeds, when present, are polyembryonic, with a slightly yellowish-white outer seed coat (RHS Yellow-White 158A), a grayish-orange (RHS Greyed-Orange 164C) inner seed coat, and grayish-yellow (RHS Greyed-Yellow 160C) colyledons.

Figure 6:
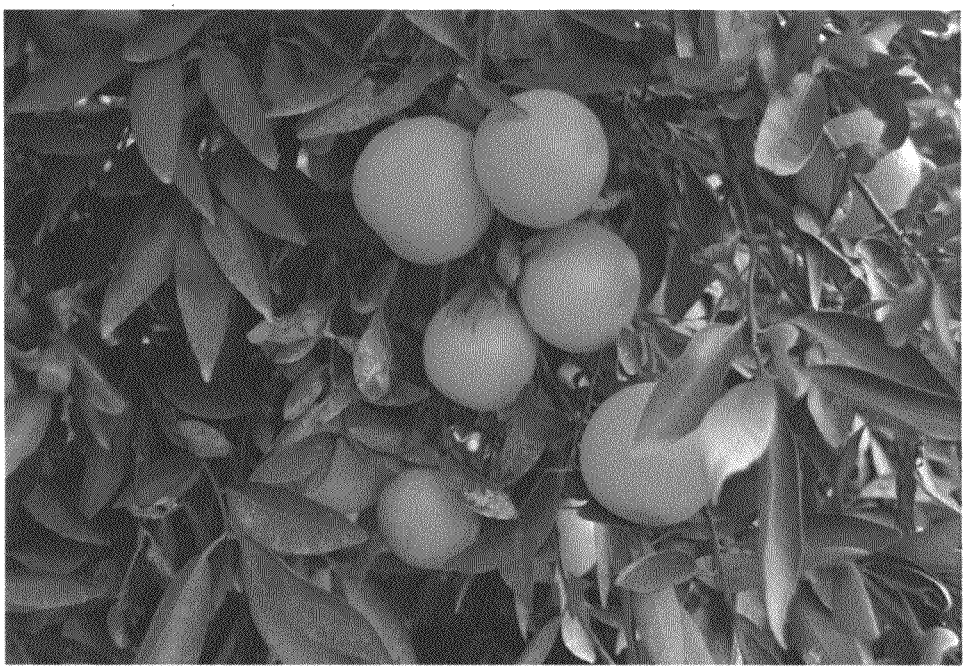
FIG. 6 shows fruit clusters of 'FairchildLS' taken at Riverside in February 2009.

Fruit production of 'FairchildLS' begins in the third year after planting, which is similar to 'Fairchild'. Fruit production on four-year-old trees averaged 28.0-49.2 kg, and on five-year-old trees averaged 41.6-64.7 kg at the fruiting trial sites (FIG. 6, Table 3). The original "mother" tree at Riverside was similar in fruit production at age four and five years (45.2 and 72.1 kg—not shown in Table 3). As the original tree aged, some alternate bearing became apparent in years seven and eight. This is similar to 'Fairchild' mandarin, which has a history of alternate bearing.

Fruit storage trials included storage of washed but not waxed fruit at 5.6° C. for up to 45 days with fruit samples taken every 15 days for analysis. Data indicates that the storage characteristics of 'FairchildLS' are very good with no measureable loss of rind quality or color, no significant loss in juice quality or deterioration in taste, and no significant indication of fungal or other disease problems over the 45 day storage period.

TABLE 2

Fruit characteristics of 'FairchildLS' mandarin at maturity

| | |
|---|---|
| 1. Fruit shape | Deep oblate |
| 2. Fruit diameter | 64.0 mm ± 3.3 |
| 3. Fruit height | 56.1 mm ± 2.3 |
| 4. Aspect ratio (height/diameter) | 0.88 |
| 5. Fruit: shape of basal end | Slightly concave (flattened at stem) |
| 6. Fruit: shape of distal end | Truncate (slightly depressed) |
| 7. Fruit: distal end areola | Present but faint (18.8 mm in diameter) |
| 8. Fruit neck | Not present |
| 9. Style | Not persistent |
| 10. Rind texture | Moderately smooth |
| 11. Oil glands | Slightly conspicuous, slightly depressed |
| 12. Rind Color | RHS Orange N25B |
| 13. Rind thickness | 3.5 mm |
| 14. Albedo thickness | 1.5 mm |
| 15. Albedo color | RHS Yellow-Orange 23C |
| 16. Rind adherence | Medium |
| 17. Rind separation | Slight |
| 18. Flesh (pulp) color | RHS Orange-Red N30D |
| 19. Flesh (pulp) texture | Moderately fine |
| 20. Number of segments | 11-12 |
| 21. Axis: structure | Semi-hollow |
| 22. Axis: size | Medium |
| 23. Navel presence | Not present |
| 24. # Seeds/fruit (mean) | 2.4 ± 0.6 (cross-pollinated conditions) |
| 25. Seed embryony | Polyembryonic |
| 26. Seed coat color | Yellow-White 158A |
| 27. Seed cotyledon color | Greyed-Yellow 160C |
| 28. Seed inner coat color | Greyed-Orange 164C |
| 29. Fruit weight | 110 g |
| 30. % Juice | 47.2% |
| 31. % Soluble solids (at maturity) | 12.6% |
| 32. % Acid (at maturity) | 1.11% |
| 33. Season of maturity | Mid-season (early January-April) |
| 34. Fruit holding ability on tree past maturity | 4-8 weeks |
| 35. Fruit quality after storage (5.6° C., 45 days) | Very Good |

TABLE 3

Crop yields for 'FairchildLS' and 'Fairchild' (control trees) at four trial sites over two years, 2006/2007, 2007/2008, and 2008/2009.

| Site | Selection | # Trees | Age in 2009 (yrs) | Root-stock | 2006/7 Mean Yield (kg) | 2006/7 Yield Range (kg) | 2007/8 Mean Yield (kg) |
|---|---|---|---|---|---|---|---|
| River-side | 'FairchildLS' | 10 | 6 | Carrizo | 40.1 | 29.8-57.9 | 48.3 |
| River-side | 'FairchildLS' | 9 | 6 | C35 | 38.8 | 27.8-45.9 | 49.2 |
| River-side | 'FairchildLS' (mother) | 1 | 11 | Carrizo | 64.8 | 64.8 | 46.3 |
| River-side | 'Fairchild' control | 2 | 11 | Carrizo | 68.5 | 62.4-74.6 | 47.7 |
| Coach-ella | 'FairchildLS' | 6 | 4 | Carrizo | * | * | 15.2 |
| Coach-ella | 'FairchildLS' | 6 | 4 | C35 | * | * | 13.4 |
| Coach-ella | 'Fairchild' control | 3 | 4 | Carrizo | * | * | 16.7 |
| Irvine | 'FairchildLS' | 6 | 5 | Carrizo | 7.2 | 0-14.6 | 28.2 |
| Irvine | 'FairchildLS' | 6 | 5 | C35 | 6.1 | 0-12.4 | 34.1 |
| Irvine | 'Fairchild' cntl | 4 | 5 | Carrizo | 18.1 | 9.4-25.2 | 37.1 |

TABLE 3-continued

Crop yields for 'FairchildLS' and 'Fairchild' (control trees) at four trial sites over two years, 2006/2007, 2007/2008, and 2008/2009.

| | | | | | | | |
|---|---|---|---|---|---|---|---|
| Lind-cove | 'FairchildLS' | 6 | 4 | Carrizo | * | * | 19.2 |
| Lind-cove | 'FairchildLS' | 6 | 4 | C35 | * | * | 23.4 |
| Lind-cove | 'Fairchild' cntl | 4 | 5 | Carrizo | 8.6 | 3.0-13.8 | 31.7 |

| Site | Selection | # Trees | Age in 2009 (yrs) | Root-stock | 2007/8 Yield Range (kg) | 2008/9 Mean Yield (kg) | 2008/9 Yield Range (kg) |
|---|---|---|---|---|---|---|---|
| River-side | 'FairchildLS' | 10 | 6 | Carrizo | 32.1-60.6 | 67.2 | 53.1-82.4 |
| River-side | 'FairchildLS' | 9 | 6 | C35 | 31.0-66.9 | 64.7 | 55.1-79.4 |
| River-side | 'FairchildLS' (mother) | 1 | 11 | Carrizo | 46.3 | 70.4 | 70.4 |
| River-side | 'Fairchild' control | 2 | 11 | Carrizo | 44.1-51.3 | 66.9 | 62.9-70.9 |
| Coach-ella | 'FairchildLS' | 6 | 4 | Carrizo | 8.1-24.4 | 32.2 | 19.3-38.1 |
| Coach-ella | 'FairchildLS' | 6 | 4 | C35 | 6.3-21.7 | 35.9 | 17.9-46.4 |
| Coach-ella | 'Fairchild' control | 3 | 4 | Carrizo | 14.1-18.7 | 29.7 | 21.8-32.0 |
| Irvine | 'FairchildLS' | 6 | 5 | Carrizo | 22.8-43.9 | 41.6 | 36.1-62.4 |
| Irvine | 'FairchildLS' | 6 | 5 | C35 | 27.8-45.9 | 43.5 | 39.8-65.9 |
| Irvine | 'Fairchild' cntl | 4 | 5 | Carrizo | 24.6-47.9 | 49.2 | 41.5-54.6 |
| Lind-cove | 'FairchildLS' | 6 | 4 | Carrizo | 10.1-27.4 | 30.1 | 18.8-36.1 |
| Lind-cove | 'FairchildLS' | 6 | 4 | C35 | 8.4-29.7 | 28.9 | 15.9-35.4 |
| Lind-cove | 'Fairchild' cntl | 4 | 5 | Carrizo | 24.4-38.7 | 35.6 | 26.4-42.0 |

* Not fruiting

TABLE 4

Seed counts (average number of seeds per fruit) for 'FairchildLS' and 'Fairchild' (control trees) at four trial sites over two years, 2007/2008 and 2008/2009.

| Site | Selection | Tree Age (yrs) | Root-stock | 2007/8 Mean Seeds/Fruit | 2007/8 Seed Count Range | 2008/9 Mean Seeds/Fruit | 2008/9 Seed Count Range |
|---|---|---|---|---|---|---|---|
| River-side | 'Fair-childLS' | 6 (10 trees) | Carrizo | 2.5 | 1.9-3.6 | 2.4 | 2.2-3.3 |
| River-side | 'Fair-childLS' | 6 (9 trees) | C35 | 2.4 | 2.1-3.3 | 2.6 | 2.0-3.0 |
| River-side | 'Fair-childLS' (mother) | 11 (1 tree) | Carrizo | 2.3 | NA | 2.4 | NA |
| River-side | 'Fairchild' control | 11 (2 trees) | Carrizo | 18.9 | 10.1-14.4 | 21.4 | 18.6-24.2 |
| Coach-ella | 'Fair-childLS' | 4 (6 trees) | Carrizo | 1.8 | 0.8-2.6 | 1.9 | 1.2-2.7 |
| Coach-ella | 'Fair-childLS' | 4 (6 trees) | C35 | 2.0 | 1.3-2.5 | 2.2 | 1.3-2.7 |
| Coach-ella | 'Fairchild' control | 4 (4 trees) | Carrizo | 17.8 | 15.2-20.4 | 18.9 | 16.1-23.2 |

TABLE 4-continued

Seed counts (average number of seeds per fruit) for 'FairchildLS' and 'Fairchild' (control trees) at four trial sites over two years, 2007/2008 and 2008/2009.

| Site | Selection | Tree Age (yrs) | Root-stock | 2007/8 Mean Seeds/ Fruit | 2007/8 Seed Count Range | 2008/9 Mean Seeds/ Fruit | 2008/9 Seed Count Range |
|---|---|---|---|---|---|---|---|
| Irvine | 'Fair-childLS' | 5 (6 trees) | Carrizo | 2.2 | 1.8-2.6 | 2.4 | 2.0-2.6 |
| Irvine | 'Fair-childLS' | 5 (6 trees) | C35 | 2.0 | 1.6-2.4 | 2.3 | 1.9-2.7 |
| Irvine | 'Fairchild' control | 5 (4 trees) | Carrizo/ C35 | 16.2 | 13.8-20.4 | 15.5 | 12.9-19.3 |
| Lind-cove | 'Fair-childLS' | 4 (6 trees) | Carrizo | 1.2 | 0.9-2.0 | 1.5 | 0.8-2.1 |
| Lind-cove | 'Fair-childLS' | 4 (6 trees) | C35 | 1.3 | 0.7-0.1.8 | 1.4 | 1.1-2.2 |
| Lind-cove | 'Fairchild' control | 4 (2 trees) | Carrizo | 14.8 | 12.3-17.3 | 15.4 | 13.9-16.9 |

TABLE 5

Mean and standard deviation (S.D.) of soluble solids, acid and solids/acid ratio for 'FairchildLS' on Carrizo and C35 citrange rootstock at four trial sites, 2007/2008 crop year.

| Site | Date | Soluble Solids % Carrrizo | S.D. | Soluble Solids % C35 | S.D. | % Acid Carrizo |
|---|---|---|---|---|---|---|
| Riverside | Dec. 17, 2007 | 11.1 | 0.37 | 10.7 | 0.46 | 1.35 |
| Riverside | Jan. 15, 2008 | 12.4 | 0.26 | 12.0 | 0.45 | 1.11 |
| Riverside | Feb. 9, 2008 | 13.3 | 0.49 | 12.9 | 0.33 | 0.98 |
| Riverside | Mar. 18, 2008 | 14.5 | 0.53 | 14.0 | 0.47 | 0.86 |
| Coachella | Dec. 17, 2007 | 12.0 | 0.31 | 10.3 | 0.36 | 0.97 |
| Coachella | Jan. 15, 2008 | 13.0 | 0.29 | 12.7 | 0.29 | 0.85 |
| Coachella | Feb. 15, 2008 | 13.4 | 0.33 | 13.0 | 0.24 | 0.81 |
| Coachella | Mar. 20, 2008 | 13.1 | 0.55 | 13.1 | 0.41 | 0.76 |
| Irvine | Dec. 17, 2007 | 11.5 | 0.68 | 11.9 | 0.39 | 1.31 |
| Irvine | Jan. 15, 2008 | 12.3 | 0.32 | 12.8 | 0.50 | 1.09 |
| Irvine | Feb. 9, 2008 | 13.5 | 0.40 | 13.4 | 0.22 | 0.95 |
| Irvine | Mar. 18, 2008 | 14.4 | 0.42 | 14.2 | 0.31 | 0.91 |
| Lindcove | Dec. 17, 2007 | 9.8 | 0.51 | 9.3 | 0.33 | 1.41 |
| Lindcove | Jan. 15, 2008 | 12.1 | 0.27 | 11.2 | 0.29 | 1.17 |
| Lindcove | Feb. 9, 2008 | 12.8 | 0.40 | 12.5 | 0.40 | 1.02 |
| Lindcove | Mar. 18, 2008 | 13.9 | 0.39 | 13.6 | 0.56 | 0.93 |

TABLE 5-continued

Mean and standard deviation (S.D.) of soluble solids, acid and solids/acid ratio for 'FairchildLS' on Carrizo and C35 citrange rootstock at four trial sites, 2007/2008 crop year.

| Site | Date | S.D. | % Acid C35 | S.D. | S/A Ratio Carrizo | S/A Ratio C35 |
|---|---|---|---|---|---|---|
| Riverside | Dec. 17, 2007 | 0.13 | 1.32 | 0.10 | 8.2 | 8.1 |
| Riverside | Jan. 15, 2008 | 0.10 | 1.19 | 0.08 | 11.2 | 10.1 |
| Riverside | Feb. 9, 2008 | 0.06 | 1.04 | 0.06 | 13.6 | 12.4 |
| Riverside | Mar. 18, 2008 | 0.08 | 0.94 | 0.05 | 16.7 | 14.9 |
| Coachella | Dec. 17, 2007 | 0.12 | 1.06 | 0.07 | 12.4 | 9.7 |
| Coachella | Jan. 15, 2008 | 0.09 | 0.94 | 0.09 | 15.3 | 13.5 |
| Coachella | Feb. 15, 2008 | 0.16 | 0.85 | 0.04 | 16.5 | 15.3 |
| Coachella | Mar. 20, 2008 | 0.10 | 0.78 | 0.09 | 18.2 | 16.8 |
| Irvine | Dec. 17, 2007 | 0.14 | 1.28 | 0.11 | 8.8 | 9.3 |
| Irvine | Jan. 15, 2008 | 0.13 | 1.17 | 0.11 | 11.3 | 10.9 |
| Irvine | Feb. 9, 2008 | 0.08 | 0.97 | 0.07 | 14.2 | 13.9 |
| Irvine | Mar. 18, 2008 | 0.08 | 0.90 | 0.08 | 15.8 | 15.8 |
| Lindcove | Dec. 17, 2007 | 0.15 | 1.46 | 0.18 | 7.0 | 7.0 |
| Lindcove | Jan. 15, 2008 | 0.11 | 1.23 | 0.12 | 10.1 | 9.1 |
| Lindcove | Feb. 9, 2008 | 0.06 | 1.09 | 0.07 | 12.5 | 11.7 |
| Lindcove | Mar. 18, 2008 | 0.06 | 1.01 | 0.08 | 14.9 | 13.5 |

TABLE 6

Comparison of 'FairchildLS' with other mid to mid-late season, low-seeded mandarins. Data for Riverside, California.

| Trait | 'FairchildLS' | 'Tango' | 'TDE3' | 'TDE4' | 'DaisySL' |
|---|---|---|---|---|---|
| Maturity | Early-January. | Late-January | Late-January | February | Early December-early January. |
| Seeds per fruit | 2.4 | 0.15 | 0.29 | 0.32 | 2.2 |
| RHS rind color | Orange N25B | Orange N25A | Orange-Red N30C | Orange-Red N30C | Orange-Red N30C |
| Rind texture | moderately smooth | smooth | papillate | smooth | very smooth |
| Fruit weight (g) | 110 | 90 | 134 | 175 | 135 |
| Fruit height/width | 0.88 | 0.81 | 0.85 | 0.78 | 0.88 |
| Alternate bearing | medium | low | medium-high | medium-high | medium |

No susceptibilities to plant or fruit diseases, or to pests, beyond those normally associated with *citrus* species have been observed.

What is claimed is:

1. A new and distinct mandarin tree having the characteristics substantially as described and illustrated herein.

* * * * *